United States Patent
Shankar et al.

(10) Patent No.: US 12,269,830 B2
(45) Date of Patent: Apr. 8, 2025

(54) PROCESS FOR PREPARATION OF TOFACITINIB AND PHARMACEUTICALLY ACCEPTABLE SALT THEREOF

(71) Applicant: INTAS PHARMACEUTICALS LTD., Gujarat (IN)

(72) Inventors: Rama Shankar, Gujarat (IN); Pareshkumar Keshavlal Patel, Gujarat (IN); Dhavalkumar Bharatbhai Vashi, Gujarat (IN); Ranjitkumar Ravatbhai Pada, Gujarat (IN); Ganesh Bhanudas Dhepe, Gujarat (IN); Viralkumar Arvindbhai Doshi, Gujarat (IN); Jaydip Ghanshyambhai Rajpara, Gujarat (IN)

(73) Assignee: Intas Pharmaceuticals Ltd., Gujarat (IN)

( * ) Notice: Subject to any disclaimer, the term of this patent is extended or adjusted under 35 U.S.C. 154(b) by 857 days.

(21) Appl. No.: 17/435,605

(22) PCT Filed: Mar. 4, 2020

(86) PCT No.: PCT/IB2020/051837
§ 371 (c)(1),
(2) Date: Sep. 1, 2021

(87) PCT Pub. No.: WO2020/183295
PCT Pub. Date: Sep. 17, 2020

(65) Prior Publication Data
US 2022/0153743 A1    May 19, 2022

(30) Foreign Application Priority Data
Mar. 13, 2019 (IN) .............................. 201921009802

(51) Int. Cl.
*C07D 487/04* (2006.01)
(52) U.S. Cl.
CPC ................. *C07D 487/04* (2013.01)

(58) Field of Classification Search
CPC ..................................................... C07D 487/04
USPC .......................................................... 544/280
See application file for complete search history.

(56) References Cited

U.S. PATENT DOCUMENTS

| | | |
|---|---|---|
| 7,265,221 B2 | 9/2007 | Blumenkopf et al. |
| 7,301,023 B2 | 11/2007 | Flanagan et al. |
| RE41,783 E | 9/2010 | Blumenkopf et al. |
| 9,670,160 B2 | 6/2017 | Bhirud et al. |

FOREIGN PATENT DOCUMENTS

| | | |
|---|---|---|
| WO | 2007/012953 | 2/2007 |
| WO | 2014/195978 | 12/2014 |
| WO | 2018/172821 | 9/2018 |

OTHER PUBLICATIONS

Aldrich, Handbook of Fine Chemicals, p. 1674 (Year: 1998).*
Patil, et al., "An Improved and Efficient Process for the Preparation of Tofacitinib Citrate", Org. Process Res. Dev. 2014, 18, 12, 1714-1720—Abstract.
International Search Report and Written Opinion issued in International Application No. PCT/IB2020/051837, Jul. 22, 2020, 8 pages.

* cited by examiner

*Primary Examiner* — Taylor V Oh
(74) *Attorney, Agent, or Firm* — HSML P.C.

(57) ABSTRACT

The present invention relates to an improved process for preparation of tofacitinib (I) and pharmaceutically acceptable salt thereof. (I)

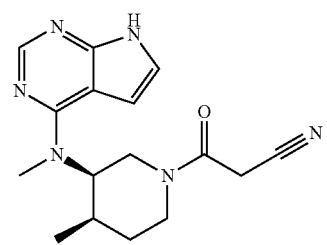

10 Claims, No Drawings

PROCESS FOR PREPARATION OF TOFACITINIB AND PHARMACEUTICALLY ACCEPTABLE SALT THEREOF

RELATED APPLICATION

This application is related to Indian Provisional Application No. IN 201921009802 filed on 13 Mar. 2020 and is incorporated herein in its entirety.

FIELD OF THE INVENTION

The present invention relates to an improved process for preparation of tofacitinib (I) and pharmaceutically acceptable salt thereof.

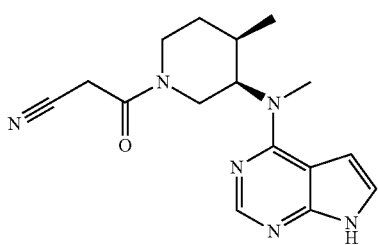

(I)

BACKGROUND OF THE INVENTION

The following discussion of prior art is intended to present the invention in appropriate technical context and allow its significance to be properly appreciated. Unless clearly indicated to the contrary, however reference to any prior-art in this specification should be construed as an admission that such art is widely known or forms part of common general knowledge in the field.

"Tofacitinib" is inhibitor of the enzyme Janus kinase 1 (JAK1) and Janus kinase 3 (JAK3), it interferes with the JAK-STAT signaling pathway. Tofacitinib is chemically known as (3R,4R)-4-methyl-3-(methyl-7H-pyrrolo[2,3-d]pyrimidin-4-ylamino)-β-oxo-1-piperidinepropanenitrile, 2-hydroxy-1,2,3-propanetricarboxylate (1:1). Its empirical formula is $C_{16}H_{20}N_6O \cdot C_6H_8O_7$. U.S. Pat. No. RE41783, U.S. Pat. Nos. 7,265,221 and 7,301,023 discloses (3R,4R)-4-methyl-3-(methyl-7H-pyrrolo[2,3-d]pyrimidin-4-ylamino)-β-oxo-1-piperidinepropanenitrile and process for its preparation.

The WO2007/012953 A2 discloses process for preparation of tofacitinib wherein chiral purity of intermediate is very poor (84% cis isomer, having 68% ee), and also the process is silent about the chirality of the final tofacitinib citrate produced by this intermediate.

WO2014/195978 A2 discloses use of acetic acid in debenzylation step of process for preparation of tofacitinib and pharmaceutically acceptable salt thereof.

Org. Process Res. Dev. 2014, 18 (12), pp 1714-1720 discloses process for preparation of tofacitinib.

In view of the above, it is therefore, desirable to provide an efficient, more economical, less hazardous and eco-friendly process for the preparation of tofacitinib and pharmaceutically acceptable salt thereof.

OBJECTS OF THE INVENTION

The main object of present invention is to provide an improved process for preparation of tofacitinib (I) and pharmaceutically acceptable salt thereof.

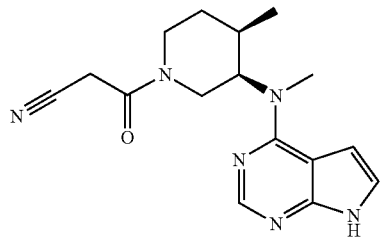

(I)

wherein, process comprises debenzylation of intermediate of formula (III) in presence of metal catalyst and pivalic acid.

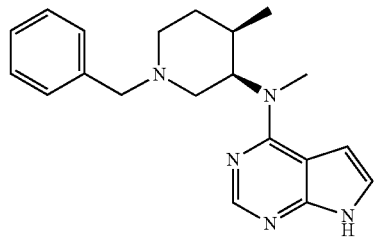

(III)

Another object of the present invention is to provide an improved process for preparation of tofacitinib citrate having dihydro impurity less than 0.2%.

Yet another object of the present invention is to provide process for preparation of tofacitinib citrate using substantially pure intermediate of formula (II).

SUMMARY OF THE INVENTION

In one aspect the present invention provides an improved process for preparation of tofacitinib (I) or its pharmaceutically acceptable salt

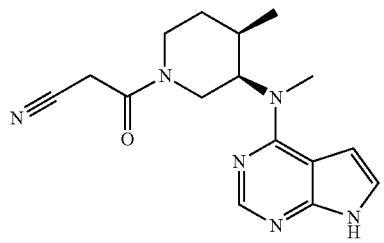

(I)

comprising, debenzylation of N-((3R,4R)-1-benzyl-4-methylpiperidin-3-yl)-N-methyl-7H-pyrrolo[2,3-d]pyrimidin-4-amine intermediate of formula (III) in presence of metal catalyst and pivalic acid.

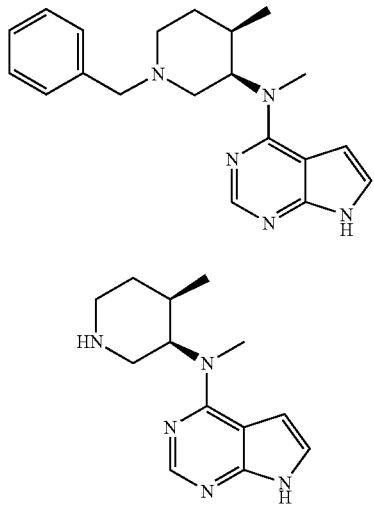

(III)

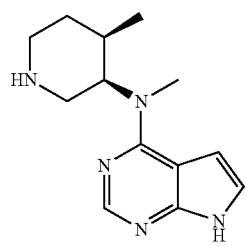

(II)

converting the resultant intermediate of formula (II) to tofacitinib citrate.

In another aspect the present invention provides an improved process for preparation of tofacitinib or its salt;

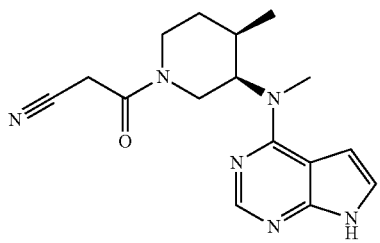

(I)

comprising, debenzylation of N-((3R,4R)-1-benzyl-4-methylpiperidin-3-yl)-N-methyl-7H-pyrrolo[2,3-d]pyrimidin-4-amine intermediate of formula (III) in presence of palladium catalyst and pivalic acid.

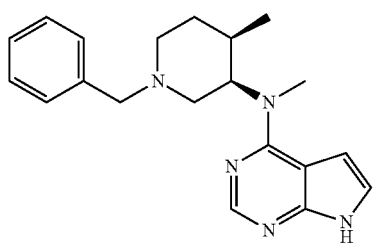

(III)

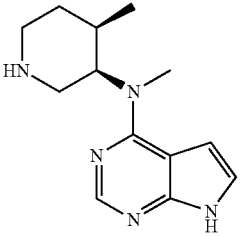

(II)

converting the resultant intermediate of formula (II) to tofacitinib citrate.

Yet another aspect of present invention is to provide a process for preparation of substantially pure tofacitinib citrate which comprises:

a) reacting compound of formula (VIII) with compound of formula (VII) to obtain compound of formula (VI);

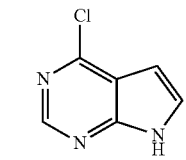

(VIII)

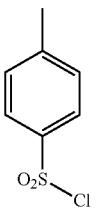

(VII)

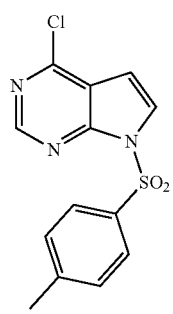

(VI)

b) reacting intermediate of formula (VI) and formula (V) in presence of water and alkali to obtain compound of formula (IV)

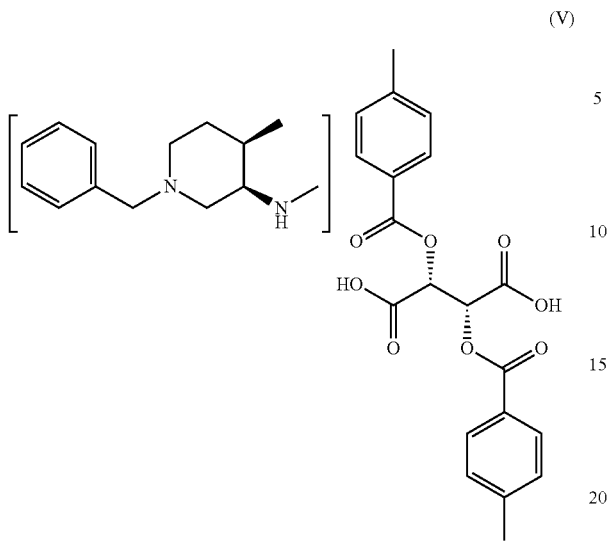

(V)

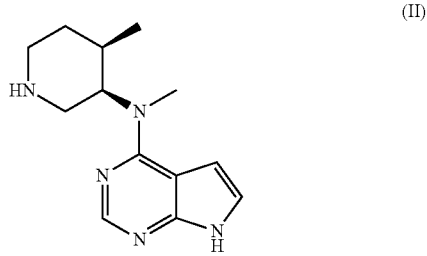 [SMILES: C[C@@H]1CCNC[C@@H]1N(C)c1ncnc2[nH]ccc12]

(II)

e) converting resultant compound of formula (II) to tofacitinib citrate f) optionally purifying to obtain substantially pure tofacitinib citrate.

Yet another aspect of the present invention is to provide a process for preparation of substantially pure tofacitinib citrate having dihydro impurity (A) less than 0.2%, preferably less than 0.05%.

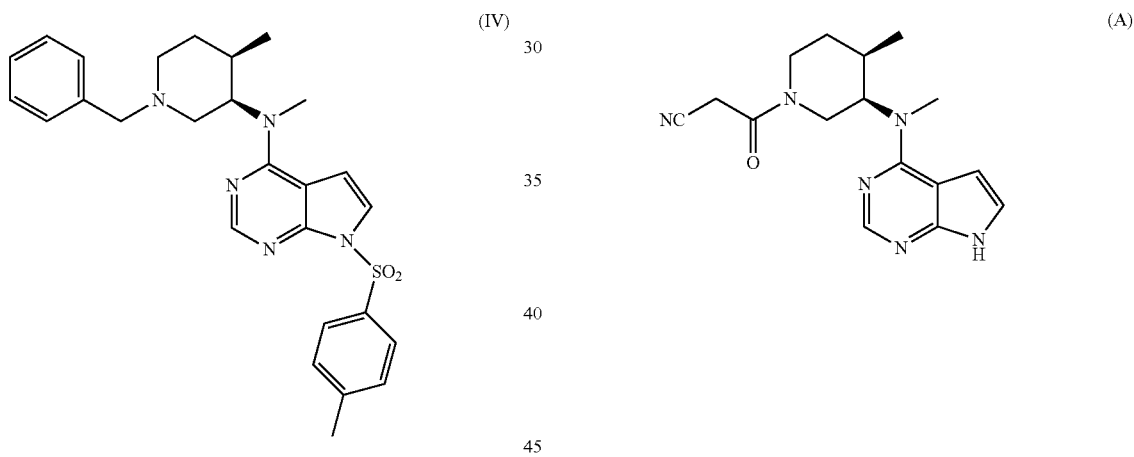

c) converting compound of formula (IV) to compound of formula (III)

d) debenzylating compound of formula (III) in presence of pivalic acid and palladium catalyst to obtain compound of formula (II); and

DETAILED DESCRIPTION OF THE INVENTION

The main embodiment of present invention provides a process for preparation of tofacitinib citrate;

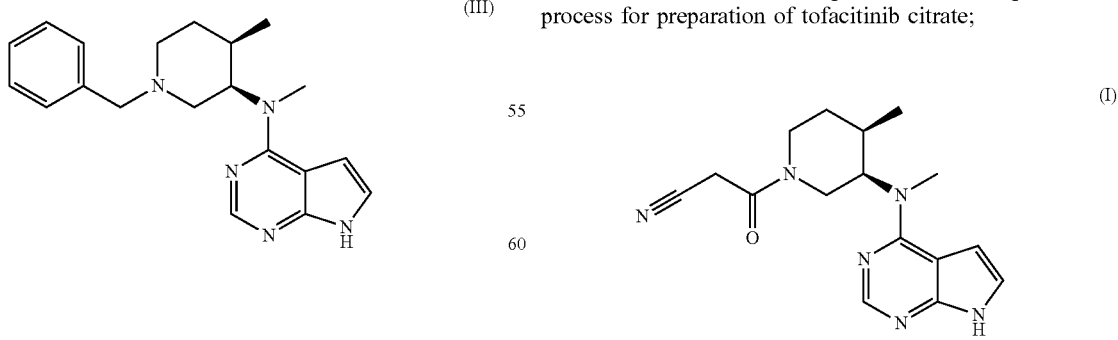

accordingly, the complete process of present invention can be represented by following scheme.

Scheme 1
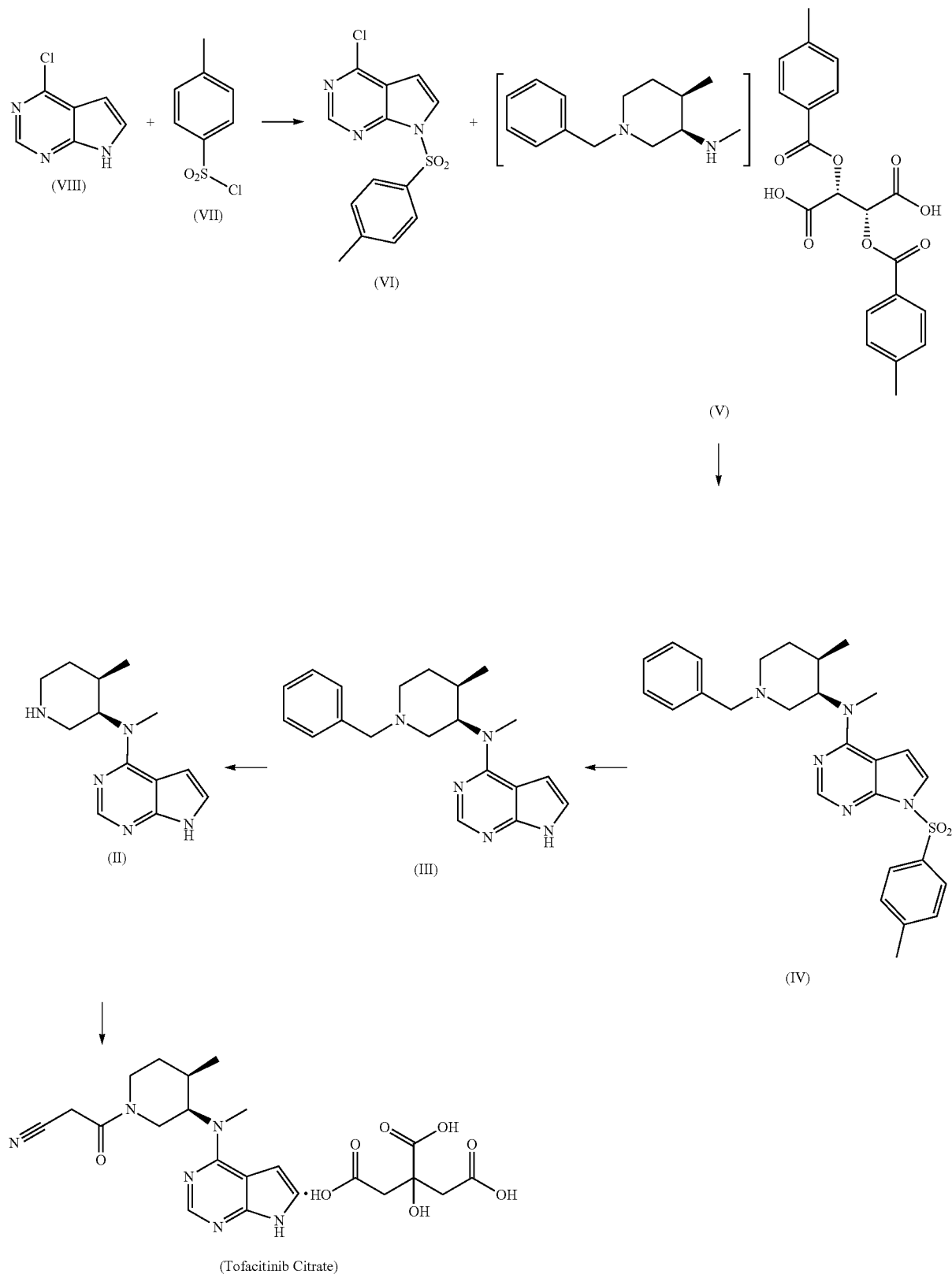

For the purpose of present invention intermediate of formula (VI) can be prepared by reacting compound of formula (VII) with compound of formula (VIII) as represented in stage I of above mentioned scheme. Which is further reacted with compound of formula (V) to obtain compound of formula (IV).

Compound of formula (IV) is hydrolyzed using alkali and water to obtain compound of formula (III), which is debenzylated by metal catalysts in presence of pivalic acid to obtain compound of formula (II). Wherein the metal catalyst can be selected from any suitable catalyst like palladium, platinum ruthenium or like. Preferably debenzylation is carried out in presence of palladium catalyst.

In an embodiment the process for preparation of intermediate of formula (II) wherein, said process is carried out in presence of pivalic acid.

The process for preparation of compound of formula (II) can be carried out in presence of suitable solvent such as aromatic hydrocarbon, alkanols or water. Suitably the reaction is carried out in presence of isopropanol, toluene, n-butanol, ethanol, water or mixture thereof.

The intermediate of formula (VI) obtained from stage I can be further converted to intermediate of formula (III) by any process known in the art. For the purpose of present invention the intermediate of formula (III) can be subjected to debenzylation in presence pivalic acid metal catalyst such as palladium. The reaction can be carried out in presence of any suitable solvent such as n-butanol, water. The intermediate of formula (II) obtained after debenzylation is converted to tofacitinib citrate. The crude tofacitinib citrate can be isolated from the reaction mixture by filtration and recrystallized to obtain substantially pure tofacitinib citrate.

TABLE 1

Summary of Debenzylation process of Tofacitinib

| Sr. No | Acid (Volume) | Solvent-1 (Volume) | Solvent-2 (Volume) | Catalyst Type | Loading | Temp. (°C.) | Pressure | Dihydro impurity by HPLC |
|---|---|---|---|---|---|---|---|---|
| 1. | Acetic acid (0.35) | Water (5) | — | 10% Pd/C | 20% | 50° C. | 10 | 0.41 |
| 2. | Pivalic acid (0.35) | Water (5) | — | 10% Pd/C | 20% | 50° C. | 10 | 0.05 |
| 3. | Acetic acid (0.35) | Water (5) | — | 20% Pd(OH)$_2$ | 20% | 50° C. | 10 | 0.17 |
| 4. | Pivalic acid (0.35) | Water (5) | — | 20% Pd(OH)$_2$ | 20% | 50° C. | 10 | 0.04 |
| 5. | Acetic acid (0.18) | Water (5) | — | 10% Pd/C | 20% | 50° C. | 10 | 0.66 |
| 6. | Pivalic acid (0.18) | Water (5) | — | 10% Pd/C | 20% | 50° C. | 10 | 0.06 |
| 7. | Pivalic acid (0.70) | Water (5) | — | 10% Pd/C | 20% | 50° C. | 10 | 0.10 |
| 8. | Pivalic acid (0.35) | Water (5) | — | 10% Pd/C | 20% | 55° C. | 10 | 0.19 |
| 9. | Pivalic acid (0.35) | Water (5) | — | 10% Pd/C | 20% | 45° C. | 10 | 0.02 |
| 10. | Pivalic acid (0.35) | Water (5) | — | 10% Pd/C | 20% | 60° C. | 10 | 0.46 |
| 11. | Trifluoro acetic acid (0.35) | Water (5) | — | 10% Pd/C | 20% | 50° C. | 10 | 2.82% |
| 12. | Acetic acid (0.2) | Water (10) | IPA (15) | 20% Pd(OH)$_2$ | 15% | 50° C. | 3-5 | 0.50 |
| 13. | Pivalic acid (0.2) | Water (5) | IPA (7.5) | 20% Pd(OH)$_2$ | 15% | 50° C. | 10 | 0.17 |

EXAMPLES

Example 1: 4-chloro-7-tosyl-7H pyrrolo[2,3-d]pyrimidine (VI)

In a three neck round bottom flask equipped with mechanical stirrer, thermometer and addition funnel, 4-methylbenzenesulfonyl chloride (86.9 gm) in acetone (300 ml) was added to the reaction mixture of 4-chloro-7H pyrrolo[2,3-d]pyrimidine (50 gm), sodium hydroxide (19.6 gm) and purified water (400 ml). The resultant reaction mixture was stirred for completion of reaction and filtered. Resulting wet-cake was washed and dried at 40-50° C. under vacuum to obtained 4-chloro-7-tosyl-7H pyrrolo[2,3-d]pyrimidine (VI).

Example 2: N-((3R,4R)-1-benzyl-4-methylpiperidin-3-yl)-N-methyl-7-tosyl-7H-pyrrolo[2,3-d]pyrimidin-4-amine (IV)

In a three neck round bottom flask equipped with mechanical stirrer, thermometer and addition funnel, 4-chloro-7-tosyl-7H pyrrolo[2,3-d]pyrimidine (60 gm) was added to the mixture of potassium carbonate (140 gm) in purified water (780 ml) and Bis-(3R,4R)-(1-benzyl-4-methyl-piperidine-3-yl)-methylamine di-p-toluoyl-L-tartarate. The reaction mixture thus obtained was heated up to 90-100° C. After completion of the reaction, reaction mixture was cooled, filtered and washed with purified water. Wet-cake thus obtained was purified with methanol (390 ml) and dried under vacuum to obtain N-((3R,4R)-1-benzyl-4-methylpiperidin-3-yl)-N-methyl-7-tosyl-7H-pyrrolo[2,3-d]pyrimidin-4-amine.

Example 3: N-((3R,4R)-1-benzyl-4-methylpiperidin-3-yl)-N-methyl-7H-pyrrolo[2,3-d]pyrimidin-4-amine (III)

In a three neck round bottom flask equipped with mechanical stirrer, thermometer and addition funnel, N-((3R,4R)-1-benzyl-4-methylpiperidin-3-yl)-N-methyl-7-tosyl-7H-pyrrolo[2,3-d]pyrimidin-4-amine (7 gm) was added to aqueous solution of Sodium hydroxide (39.16 gm). Reaction mixture was heated to 95-100° C. and stirred. After completion of reaction, reaction mixture was cooled to 25-30° C. and filtered. Resulting wet-cake was washed with water and dried under vacuum to obtain N-((3R,4R)-1-benzyl-4-methylpiperidin-3-yl)-N-methyl-7H-pyrrolo[2,3-d]pyrimidin-4-amine.

Example 4: N-methyl-N-((3R,4R)-4-ethylpiperidin-3-yl)-7H-pyrrolo[2,3-d]pyrimidin-4-amine (II)

In a three neck round bottom flask equipped with mechanical stirrer, thermometer and addition funnel, N-((3R,4R)-1-benzyl-4-methylpiperidin-3-yl)-N-methyl-7H-pyrrolo[2,3-d]pyrimidin-4-amine (10 gm) and catalytic amount of pivalic acid was added to purified water (50 ml), to the reaction mixture 10% Pd/C was added. The resulting reaction mixture was treated with hydrogen. After completion of reaction catalyst was filtered and washed with water. Filtrate thus obtained was basified with aqueous sodium hydroxide and product was extracted with n-butanol to obtain N-methyl-N-((3R,4R)-4-ethylpiperidin-3-yl)-7H-pyrrolo[2,3-d]pyrimidin-4-amine.

Example 5: Tofacitinib Citrate (Crude)

In a three neck round bottom flask equipped with mechanical stirrer, thermometer and addition funnel, N-methyl-N-((3R,4R)-4-ethylpiperidin-3-yl)-7H-pyrrolo[2,3-d]pyrimidin-4-amine (9.5 gm) was added to n-butanol (45 ml). To the resulting solution ethyl cyanoacetate (13 gm) and 1,8-diazabicyclo[5.4.0]undec-7-ene (6 gm) were added and maintained at 40-50° C. After completion of reaction aqueous citric acid solution was added and stirred. Solid thus obtained was cooled and washed with n-butanol then dried to obtain tofacitinib citrate.

Example 6: Tofacitinib Citrate (Purification)

In a three neck round bottom flask equipped with mechanical stirrer, thermometer and addition funnel, Tofacitinib crude thus obtained (10 gm) was dissolved in water (300 ml) at 80-90° C. Charcoal (0.5 gm) was added to the reaction mixture and stirred for 30 min. Charcoal was filtered and washed with hot water. Filtrate thus obtained was cooled to room temperature for 5-6 hr. and filtered. Solid thus obtained was washed with acetone and dried to obtain substantially pure tofacitinib citrate.

We claim:
1. A process for preparing a tofacitinib having formula (I) or a pharmaceutically acceptable salt thereof

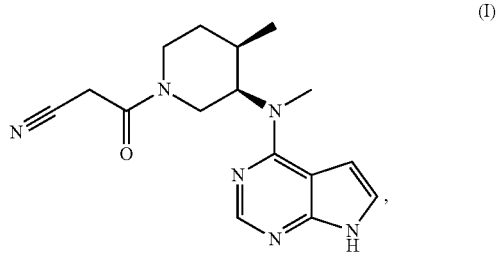 [SMILES: C[C@@H]1CCN(C(=O)CC#N)C[C@@H]1N(C)c1ncnc2[nH]ccc12]

comprising:
debenzylating N-((3R,4R)-1-benzyl-4-methylpiperidin-3-yl)-N-methyl-7H-pyrrolo[2,3-d]pyrimidin-4-amine having formula (III) in a presence of a metal catalyst and pivalic acid so as to obtain a compound having formula (II);

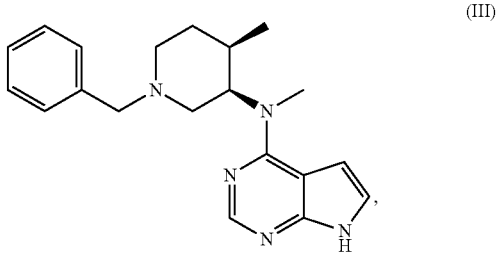

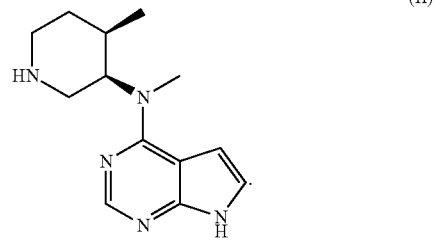

2. The process according to claim 1, wherein the metal catalyst is selected from the group consisting of palladium, platinum, and ruthenium.

3. The process according to claim 1, further comprising reacting the compound having the formula (II) with ethyl cyanoacetate, thereby converting the compound having the formula (II) to the tofacitinib having the formula (I) by coupling the compound having the formula (II) with the ethyl cyanoacetate, wherein the tofacitinib having the formula (I) comprises less than 0.2% of an impurity having formula (A)

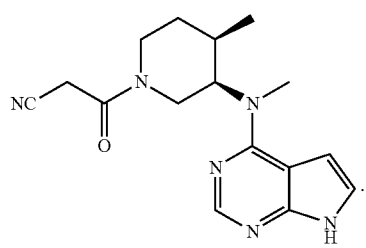
(A)

4. The process according to claim 3, wherein the tofacitinib having the formula (I) comprises less than 0.05% of the impurity having the formula (A).

5. The process according to claim 1, further comprising:

reacting the compound having the formula (II) with ethyl cyanoacetate, thereby converting the compound having the formula (II) to tofacitinib having the formula (I) by coupling the compound having the formula (II) with the ethyl cyanoacetate, wherein the tofacitinib having the formula (I) comprises less than 0.2% of an impurity having formula (A); and reacting the tofacitinib having the formula (I) comprising the impurity having the formula (A), with citric acid to obtain a citrate salt of the tofacitinib having the formula (I)

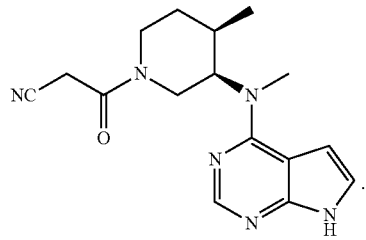
(A)

6. The process according to claim 1, further comprising;

reacting the compound having the formula (II) with ethyl cyanoacetate and citric acid so as to obtain tofacitinib citrate comprising less than 0.2% of an impurity having formula (A)

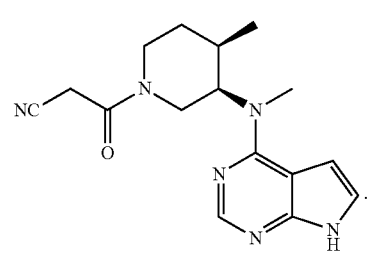
(A)

7. The process according to claim 1, wherein the debenzylation is carried out in a presence of a solvent selected from the group consisting of aromatic hydrocarbons, alkanols, water, and a mixture thereof.

8. The process according to claim 7, wherein the solvent is selected from the group consisting of toluene, xylene, isopropanol, n-butanol, methanol, ethanol, water, and a mixture thereof.

9. The process according to claim 1, wherein the tofacitinib having the formula (I) or the pharmaceutically acceptable salt thereof comprises less than 0.2% of a dihydro impurity having formula (A)

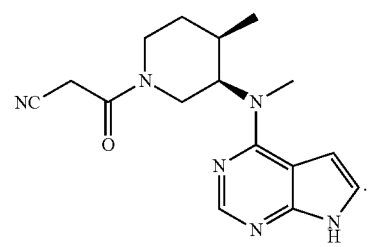
(A)

10. A tofacitinib having formula (I) or a pharmaceutically acceptable salt thereof comprising greater than 0% and less than 0.2% of a dihydro impurity having formula (A)

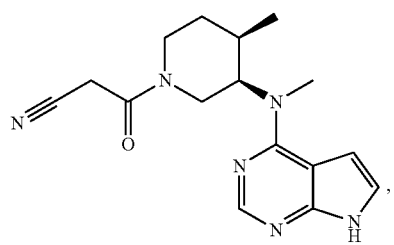
(II)

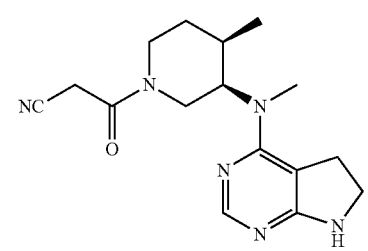
(A)

wherein the tofacitinib having the formula (I) or the pharmaceutically acceptable salt thereof is obtained by a process that comprises;

debenzylating a compound having formula (III) in a presence of pivalic acid and a palladium catalyst so as to obtain a compound having formula (II);

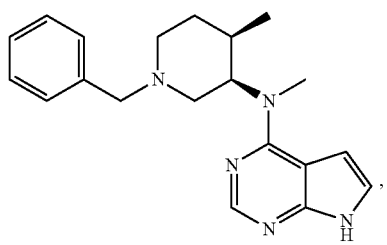
(III)

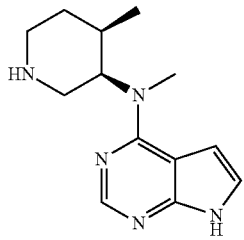
(II)

reacting the compound having the formula (II) with ethyl cyanoacetate, thereby converting the compound having the formula (II) to tofacitinib having the formula (I) by coupling the formula (II) with the ethyl cyanoacetate, wherein the tofacitinib having the formula (I) comprises less than 0.2% of the dihyro impurity having the formula (A); and reacting tofacitinib having the formula (I) with citric acid so as to obtain a citrate salt of the tofacitinib having the formula (I).

* * * * *